United States Patent [19]

Yang et al.

[11] Patent Number: 4,531,324
[45] Date of Patent: Jul. 30, 1985

[54] PLANT TISSUE CULTURE DEVICE

[75] Inventors: Ning-Sun Yang, Verona; Alan Paau, Middleton, both of Wis.

[73] Assignee: Agracetus, Middleton, Wis.

[21] Appl. No.: 540,020

[22] Filed: Oct. 7, 1983

[51] Int. Cl.³ .............................................. A01G 25/00
[52] U.S. Cl. ............................................ 47/81; 47/59
[58] Field of Search .................. 47/81, 59, 60, 61, 39, 47/66

[56] References Cited

U.S. PATENT DOCUMENTS

| 911,149 | 2/1909 | Moore | 47/39 |
|---|---|---|---|
| 2,241,699 | 5/1941 | Cooper | 47/59 |
| 2,406,439 | 8/1946 | Pratt | 47/79 |
| 2,554,302 | 5/1951 | Keskitalo | 47/81 |
| 2,775,113 | 10/1939 | Fischer | 47/59 |
| 4,224,765 | 9/1980 | Song | 47/66 |
| 4,299,054 | 11/1981 | Ware | 47/81 |
| 4,343,109 | 8/1982 | Holtkamp | 47/39 |

FOREIGN PATENT DOCUMENTS 2069804  9/1981  United Kingdom ................... 47/81

Primary Examiner—Robert A. Hafer
Assistant Examiner—Bradley M. Lewis
Attorney, Agent, or Firm—Albert P. Halluin; Elliott L. Fineman; Nicholas J. Seay

[57] ABSTRACT

A plant tissue culture device is disclosed for the culturing of a plurality of plant cell tissue cultures or callus cultures on a liquid medium. The cultures are maintained in culture wells on a culture plate and a porous wick is used to transport nutrient medium to the cultures from a supply of medium in a medium vessel underneath the culture plate.

5 Claims, 3 Drawing Figures

PLANT TISSUE CULTURE DEVICE

TECHNICAL FIELD

The present invention relates to the general subject matter of trays or containers for maintaining cultures of live tissues, and relates, in particular, to a device for the in vitro culture of plant cell tissues or callus cultures.

BACKGROUND OF THE INVENTION

It has become common place in the technology of plant husbandry and plant research to cultivate plant tissues in vitro for a wide variety of purposes. The purposes include conducting experiments with plant tissues, genetically engineering plant tissues, the asexual reproduction of commercial flowering and decorative plants, and other similar purposes. It is generally known that certain nutrient components such as salts, vitamins and hormones are necessary to foster plant tissue growth in or on a culture medium and various different mechanisms are used to provide plant tissues grown in culture with such requirements.

Currently, the vast majority of plant tissue culture methods employ a solid phase medium as a growth substrate for plant calli and plant tissue explants. The typical solid or semi-solid medium utilized is an agar type substrate, such as that described in Gamborg and Shyluk, "Nutrition, Media and Characteristics of Plant Cell and Tissue Cultures", *Plant Tissue Culture: Methods and Application in Agriculture*, Academic Press, 1981; Helgeson, "Plant Tissue and Cell Suspension Culture", *Tissue Culture Methods for Plant Pathologists*, Blackwell Scientific Publishing, 1980, page 19. Using an agar substrate, the plant tissues themselves are placed directly on the solid medium which is dosed with the nutrient requirements of the plant cells growing thereon. It is recognized, however, that many such nutrients and also cellular metabolites do not diffuse as effectively across a solid or semi-solid agar matrix as compared with their rates of diffusion in aqueous solution. Therefore, around plant cell cultures grown on a solid phase agar substrates, chemical gradients of both nutrient components and cellular metabolites tend to be generated in the agar layer surrounding the cultured plant tissues. These gradients can cause undesirable or imbalanced chemical conditions in the environment immediately about the growing plant callus or tissue which can sometimes interfere with effective continuous growth of the cultured plant tissues. The deleterious effects of the development of these gradients can be partially reduced by frequent transfer of the callus or culture tissues to fresh culture plates. This practice is, however, relatively expensive and laborious since the tissue cultures must be individually transferred by hand from new to old plates. Furthermore, the continuous growth of the cultured specimens is often disturbed, sometimes irreparably, because of this manipulation, and the handling of the cultures increases the chance of microbial contamination of the growing cultures and their media.

One other previously used method of fostering the growth of plant cell cultures or calluses is to grow the cultures on filter paper bridges folded and inserted into a culture vessel, such as a test tube, supplied with a quantity of liquid nutrient medium. The liquid medium travels up the filter paper bridge by capillary action and thus provides nutrients to the plant tissues or callus cultures grown on the filter paper bridge. This method does provide a better exchange of nutrients between the culture and the medium than does the use of solid or semi-solid supports like agar and agarose. This method is described in the literature by Tokumasu and Kato "Variation of Chromosome Numbers and Essential Aid Components of Plants Derived from Anther Culture of the Diploid and the Tetraploid in Pelargonium Rozeum", *Euphytica*, 28; 329, 1978, and by Pillai and Hildebrandt, "Induced Differentiation of Geranium Plants from Undifferentiated Callus In Vitro", *Amer. J. Bot.*, 56: 52, 1969. The problem with the use of the filter paper bridge and test tube method is that the bridge portion of the paper holding the callus does not have a firm support and therefore the filter paper bridges have to be carefully folded so that the legs of the filter paper wicks are positioned along the walls of relatively narrow culture vessels, like test tubes, to provide a support for the tissue culture. This design makes it impractical to culture a large number of samples under identical conditions in one vessel, since a different vessel must be provided for each of the cultures. A problem also occurs in that only a certain filter paper materials are suitable for use in this method, since when the paper bridge is wet, the combined weight of the absorbed liquid nutrient medium and the cultured plant tissue specimen can collapse the bridge. Even for commonly available types of filter paper, the use of the filter paper bridge method is limited to cultures of small size since the growing culture can often by itself collapse the bridge thereby dumping the culture into the nutrient medium. It is also common, because there is not regulatory mechanism for the removal of excess liquid, for the tissues cultivated under such a method to become overly soaked with liquid medium to thereby suffer from inadequate gas exchange with the atmosphere to the detriment of the culture. Thus while this method is useful in a laboratory on small scale experiments, the adaptation of such a system to the larger scale cultivation of plant tissue cultures is not practical.

It has also been known previously in the technology that whole plants, as opposed to plant tissue cultures or callus cultures, can be cultivated in apparatus wherein the liquid nutrient requirements of the plant are met by use of a wick providing capillary action from a nutrient medium located beneath the plant. For example, the disclosure of U.S. Pat. No. 4,299,054, to Ware, describes a hydroponic assembly for growing plants which includes a wafer upon which the plant is grown. One or more wicks are provided depending from the wafer into a nutrient media provided in the apparatus so that liquid nutrient media travels by capillary action up the wick to saturate the wafer to provide liquid requirements for the plants needs. Such a system, while possibly satisfactory for the growth of an intact plant including roots, is not satisfactory for the growth of a plant explant tissue cultures or callus cultures since such a system requires root growth into the liquid culture medium for continued plant viability.

SUMMARY OF THE INVENTION

The present invention is summarized in that a plant tissue culture device includes a medium vessel holding a supply of liquid nutrient medium for the plant tissue culture; a culture plate mounted in the culture vessel above the liquid medium, the culture plate having at least one pair of openings therein; at least one culture well formed on the culture plate to contain a plant tissue culture therein; and at least one continuous wick of porous material folded so as to have a central culture host portion and a pair of depending legs, the culture host portion located in the culture well and receiving the plant tissue culture thereon, supported firmly on the culture plate, while the legs extend through the openings in the culture plate to depend into the liquid medium in the vessel so that liquid medium will be transported to the culture medium portion in the culture well by capillary action to sustain any plant tissue on the culture portion.

It is an object of the present invention to provide a plant tissue culture device which is specifically adapted to facilitate the cultivation and maintenance of plant tissue cultures and plant callus cultures on liquid medium.

It is an object of the present invention to provide such an apparatus which is capable of external automatic operation so as to avoid the need for continuous manual maintenance.

It is yet another object of the present invention to provide such an apparatus which also facilitates the recovery of plant metabolites or exudates from the tissue cultures or plant callus cultures.

Other objects, advantages, and features of the present invention will become apparent from the following specification when taken in conjunction with the accompanying drawings.

DESCRIPTION OF THE PREFERRED EMBODIMENT

Figure 1:
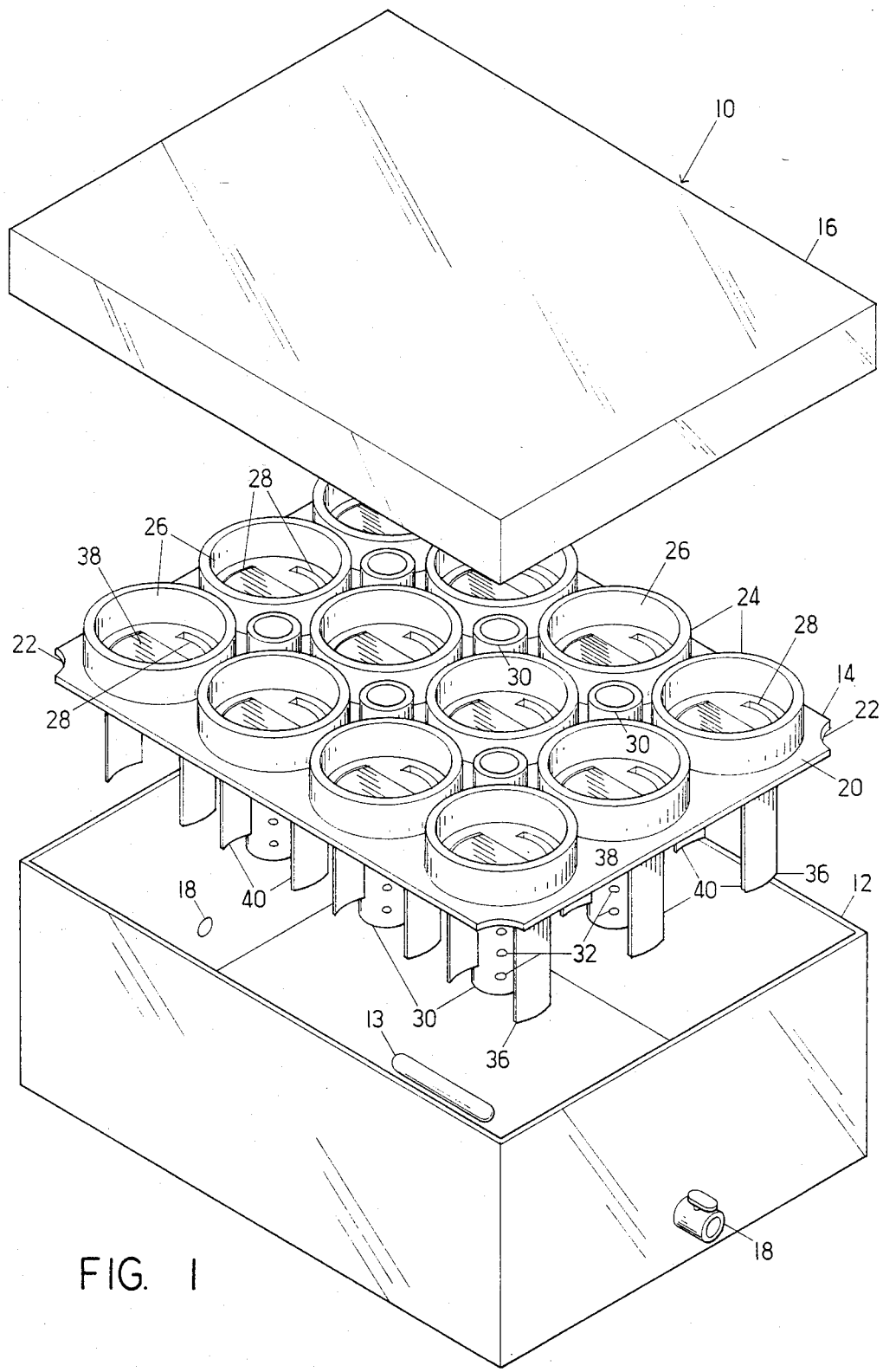
FIG. 1 is a perspective exploded view of a plant tissue culture device constructed in accordance with the present invention.

Shown in FIG. 1, and generally indicated at 10, is a plant tissue culture device constructed in accordance with the present invention. In the exploded view of the device as illustrated in FIG. 1, the three main structural components of the tissue culture device 10 are shown separated. The bottom of the tissue culture device 10 is a medium vessel 12. Into the medium vessel 12 is inserted a culture plate assembly 14, and a cover plate 16 is adapted to fit over and cover the medium vessel 12 with the culture plate assembly 14 therein. Each of these components is adapted to be constructed from lightweight, rigid, preferably transparent materials, such as polycarbonate plastics.

The medium vessel 12 is a large rectangular receptacle adapted to receive a quantity of liquid culture medium therein. At each end of the medium vessel are a respective one of a pair of inlet and outlet connectors 18 which are adapted to being connected to standard laboratory hosing for introducing media fluid into and draining fluid out of the medium vessel 12. The medium vessel should be fluid-tight and may be constructed of any suitable material, but, as stated above, it is preferably constructed of transparent synthetic resin material. A magnetically operable stirrer 13 is placed in the bottom of the medium vessel so that the medium in the vessel 12 can be stirred under external magnetic control.

The culture plate assembly 14 is designed in size so as to fit into and to generally extend completely across the interior of the medium vessel 12. The culture plate assembly 14 includes a planar culture plate 20 which is largely rectangular in shape and size and adapted to be only very slightly smaller than the interior horizontal rectangular size of the medium vessel 12. The four corners of the culture plate 20 are cut away to provide arcuate access ports 22. The access ports 22 may be of any suitable shape, such as the semi-circular cut-outs illustrated in the culture plate assembly 14 of FIG. 1, but are preferably of sufficient size to allow tubing, pipets, or other standard laboratory apparatus to reach past the culture plate assembly 14 into the bottom of the medium vessel 12, even when the culture plate assembly 14 rests inside of the medium vessel 12. Mounted on the culture plate 20 are a plurality of culture well walls 24. Each of the culture well walls 24 is formed as an upstanding cylinder defining therein a culture well, indicated at 26. The culture well walls 24 are preferably sufficiently high so as to accommodate therein the entire tissue culture which it is desired to cultivate or maintain within the device 10. On the bottom of each of the culture wells 26 are a plurality of openings 28 cut entirely through the culture plate 20. In the embodiment of the device as illustrated in FIG. 1, there are four of the openings 28 each of which is in an arcuate shape so as to form an interrupted circle centered in the central portion of the bottom of the culture well 26.

Included in the culture plate assembly 14 are a plurality of upstanding vertical supports 30. Each of the upstanding vertical supports 30 extends through suitable appropriate hole provided in the culture plate 20. Each of the vertical supports 30 is a hollow cylinder, preferably again formed of a rigid synthetic resin material, which has a plurality of spaced pairs of adjustment holes 32 provided extending horizontally therethrough. A peg 34 is provided with each of the vertical supports 30 which can be inserted through a selected pair of adjustment holes 32 with the culture plate 20 resting on the pegs 34 so as to support the culture plate 20 at a selected adjustable height relative to the vertical supports 30. Alternatively, if a fixed height for the culture plate 20 was acceptable, the culture plate 20 could be fastened permanently to the medium vessel 12 at that appropriate fixed height.

Also included in the culture plate assembly 14 are a plurality of wicks 36. In the embodiment illustrated in FIGS. 1 and 2, there is one wick 36 provided for each of the culture wells 26 although it is possible, as illustrated in the embodiment of FIG. 3, to have one wick for the entire culture plate assembly 14. In the embodiment of FIG. 1, however, each culture well 26 has associated with it a single wick 36 formed of filter paper or other highly porous sheet material capable of fostering transport of liquid by capillary action when placed partially in a fluid medium. Each of the wicks 36 is bent twice to form a culture host portion 38 located in the bottom of the respective culture well 26, resting firmly on the culture plate 20, and a pair of depending legs 40 each extending through one of the openings 28 and downwardly draped from the culture plate 20 into the liquid medium in the vessel 18. The elongated arcuate shape of the openings 28 allow easy passage of the legs 40 of the wick 36 therethrough. The wick 36 is preferably sized and folded such that each of the legs 40 will depend downwardly near to the bottom of the medium vessel 12 when the culture plate assembly 14 is placed inside of the medium vessel. To facilitate the flow and exchange of nutrient medium solution through the wicks 36, the medium can be stirred or the entire device can be shaken or swirled to maintain a homogeneous medium.

The cover plate 16 is a plate adapted in size so as to fit over the top of the medium vessel 12 enclosing the culture plate assembly 14 entirely therein. Preferably the cover plate 16 is again constructed of transparent synthetic resin material, such as a polycarbonate, although in some circumstances it may be desirable to have the cover plate constructed of an opaque material where it is desired to avoid photosynthesis in plant cultures being maintained or cultivated in the culture device 10.

Figure 2:
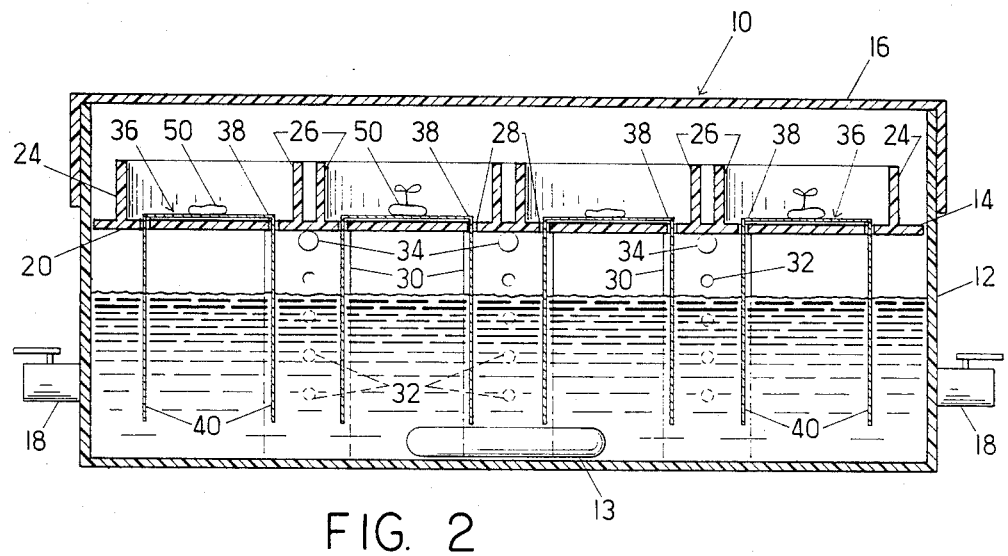
FIG. 2 is a longitudinal elevational cross-sectional view of the device of FIG. 1 assembled.
Figure 3:
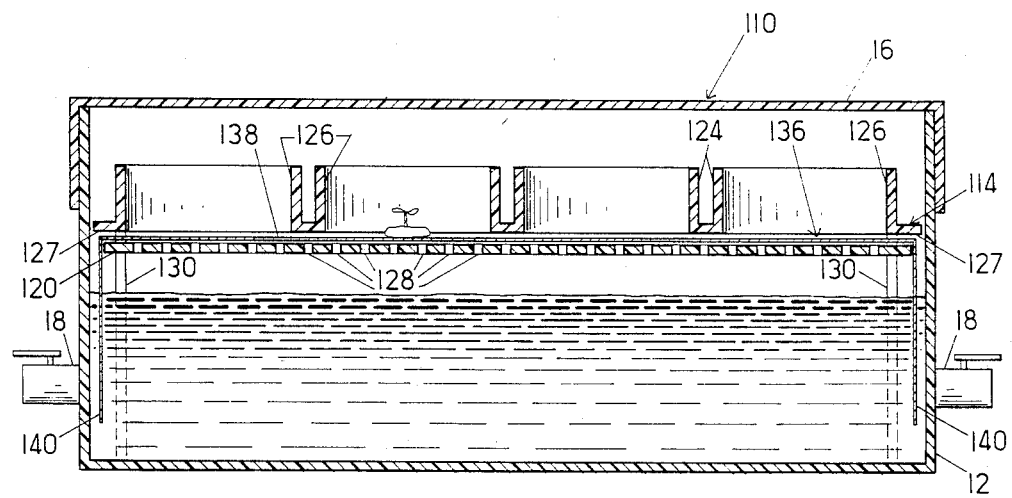
FIG. 3 is a longitudinal cross-sectional view, similar to FIG. 2, of an alternative embodiment of a plant tissue culture device constructed in accordance with the present invention.

Illustrated in FIG. 2 is a cross-sectional view of the assembled tissue culture device 10 as used in operation. The culture plate assembly 14 is mounted inside the medium vessel 12 in such a fashion that the culture plate 20 itself is mounted parallel to and above the level of the liquid contained in the medium vessel 12. The culture plate 20 rests securely in position by resting on a series of pegs 34 which are inserted through a corresponding set of adjustment holes 32 in each of the vertical supports 30. By changing the appropriate pairs of adjustment holes 32 into which the pegs 34 are inserted, the height at which the culture plate 20 is mounted in the medium vessel 12 can be adjusted. As can be clearly seen in FIG. 2, each of the wicks 36 is folded twice at right angles so as to form generally three portions. The culture host portion 38 rests on the top of the culture plate 20 and the bottom of the culture well 26. In this fashion the culture host portion 38 is firmly supported in a firm planar surface which forms a rigid and secure base onto which plant tissues can be deposited and grown. Depending downward from the culture host portion 38 are the legs 40 which are folded at approximately perpendicularly to the culture host portion 38. The legs 40 depend downwardly to be immersed into the liquid medium contained inside of the medium vessel 12.

In its operation, the tissue culture device the present invention is used to foster the growth plant tissues in a culture sustained by liquid medium. As can be seen in FIG. 2, plant tissues 50 are placed on top of the culture host portion 38 of each of the wicks 36 contained in each of the culture wells 26. Liquid nutrient medium from the reservoir contained in the medium vessel 12 as absorbed by capillary action up the legs 40 of each of the wicks 36. Thus the culture host portion 38 of each of the wicks 36 eventually dampens with culture medium and the plant tissue culture 50 growing on the culture host portion 38 can obtain their liquid nutrient requirements from the constantly replenished liquid in the culture host portion 38. Excess dampening of the cultures is prevented by the provision of the excess openings 28 provided through the culture plate 20 in each of the culture wells 26. Should the capillary action provided by the wicks 36 succeed in bringing too much liquid into the culture well 26, the excess liquid drains through the extra openings 28 back into the reservoir of liquid medium contained in the medium vessel 12. Thus oversaturation of the tissue culture 50 in each of the culture wells 26 is avoided. Also the level of moisture to which the cultures are exposed can be adjusted by changing the distance between the culture plate 20 and the level of the liquid in the medium vessel 12. This can be done either by adjusting the level of the culture plate 20 upward or downward on the vertical supports 30 or by raising or lowering the liquid level in the vessel 12 through liquid exchange through the inlet or outlet connectors 18.

The inlet and outlet connectors 18 allow for automatic additions to, removals from, adjustment of level of, or complete changing of the liquid nutrient medium contained in the medium vessel 12. It is envisioned in a large-scale facility for culturing plant tissues that the operation of many culture devices 10 would be under automatic control in a large-scale system so that periodically, on an automatically timed or on a continuous feedback responsive basis, additional nutrient medium would be introduced into or removed from the medium vessels 12 through the inlet and outlet connectors 18. A mariotte flask reservoir system is an example of an efficient system for supplying liquid to and maintaining the liquid level in the medium vessel 12 of the present invention independent of the rate of evaporation or transpiration losses. The magnetic stirrer 13 is provided in the bottom of the medium vessel 12 so that automatic stirring of the liquid medium contained in the medium vessel 12 can be accomplished if the nutrient medium contained substances which would otherwise stratify within the vessel.

The apparatus according to the present invention provides several advantages of prior art devices. One of the most significant advantages the present device provides over the now commonly used paper filter bridge structure is that the carrying capacity of the culture wells 26 of the present invention is significantly higher than that obtainable by a paper filter bridge alone contained in a test tube since the culture host portion 38 rests firmly on a fixed and rigid surface, i.e. the culture plate 20. Furthermore, the provisions for the extra openings 28 allow excess fluid to be drained from each of the plant cell culture wells 26 so as to avoid oversaturation of the cultures. Since the liquid nutrient medium in the medium vessel 12 can be supplemented or removed or have its level adjusted without disturbing the tissue cultures being maintained in the culture wells 26, i.e. either by use of the inlet and outlet valves 16 or by inserting appropriate liquid conduits through the access ports 22 provided in the corners of the culture plate 20, there is no need to disturb the culture when adding additional nutrient medium, when changing the medium in accordance with the plants needs during growth phases, or when removing the medium to retrieve exudates or metabolites therefrom.

It is particularly envisioned that the apparatus according to the present invention will be particular useful for the collection of plant exudates and metabolites from plant cell tissues grown in culture. Much experimentation is currently being undertaken to develop genetically engineered plant tissues which can be grown in culture and which exude or metabolize certain desirable substances. If the plant tissue cultures grown within the culture device 10 which exude desirable substances, the chemical substances would diffuse down the wick 36 to the liquid nutrient medium contained in the medium vessel 12. Since the medium in the medium vessel 12 can be periodically removed and processed through appropriate separation steps to remove the desired exudates from the medium, any desired exudates or metabolites which are produced by any plant cell tissue cultures grown on the culture device 10 can be recovered easily, and under automatic control, something heretofore not possible in the art.

Furthermore the culture device of the present invention allows a large number of plant tissue cultures to be exposed to identical growth conditions both in terms of temperature and light and also in terms of chemical environment since all the tissues in a single culture device will by definition be exposed to the same conditions. This feature can never be completely assured in a system in which the cultures are kept in separate containers, i.e. when they are kept in individual test tubes.

Shown in FIG. 4 is an alternative embodiment of a plant tissue culture device, generally indicated at 110, constructed in accordance with the present invention. Like parts in the plant tissue culture device 110 have been given numerals similar to those in the plant tissue culture device 10. The plant tissue culture device 110 includes a medium vessel 12 and a top cover 16 which were identical to those in the tissue culture device 10. The culture plate assembly 114 of the tissue culture device 10 is somewhat modified from that in the embodiment of FIGS. 1 and 2. In the plate assembly 114 the culture well walls 128 are raised up above the culture plate 120 to define a continuous longitudinal slot 115 is underneath each of the culture wells 126 formed inside the walls 28. A pair of openings 127 are provided at each end of the slot 115. The openings 128 provided in the culture plate 120 are numerous in character and are located below the longitudinal slot 115. The culture plate assembly 114 rests above the bottom of the medium vessel 12 on four simple mechanical legs 140. In the tissue culture device 110 there is only one wick 136 which has an extremely large culture host portion 138 which extends completely through the slot 115 and underneath each of the raised culture well walls 128 in the culture plate assembly 114. The legs 140 of the wick 136 are bent downward at the ends of the tissue culture plate assembly 14 to extend through the openings 127 to depend downwardly into liquid medium contained in the medium vessel 12.

In its operation, the tissue culture device 110 of FIG. 3 functions in a fashion identical to the tissue culture device 10 of FIGS. 1 and 2. Liquid nutrient medium is absorbed by the wick 136 and travels up the legs 140 by capillary action to soak the culture host portion 138. The culture host portion 138, which extends continuously along the bottom of all of the culture wells 126, is drained by the openings 128 provided in the culture plate 120 just beneath the culture host portion 138. The culture plate 120 still supports the culture host portion 138 so that the tissue cultures are firmly supported thereon. This structure provides all of the advantages inherent in the tissue culture device 10. For extremely large plates constructed according to this embodiment it would be particularly helpful to gently continuously swirl the culture device on top of a shaker to assure good fluid contact with the filter paper to facilitate even exchange of growth medium.

As an additional modification of any embodiment of the present invention, it is possible to utilize multiple layer wicks in the device of the present invention in which various nutrient or non-absorbent layer laminations can be combined with porous layers. One advantageous lamination would be to cover the culture host portion of the wick or wicks with a thin layer of agarose gel, perhaps 1 mm thick. This layer could serve as an advantageous growth substrate for some plant tissue cultures without significantly interferring with nutrient transport.

It is understood that the present invention is not limited to the particular construction and arrangement of parts disclosed herein, but embraces all such modified forms thereof as come within the scope of the following claims.

What is claimed is:

1. A plant tissue culture device specifically adapted for use with plant calli and other plant tissue cultures generally without roots comprising
a medium vessel for holding a supply of liquid plant tissue culture medium therein;
liquid inlet and outlet means for connecting the medium vessel to sources and drains of medium so that the level of the liquid medium can be changed to vary the distance between the liquid level and the culture plate or to add to, remove from, or exchange liquid medium;
a removable rigid culture plate mounted in and extending across the medium vessel above the level of the liquid medium therein, the culture plate provided with at least one access port in one of its corners to allow access to the medium in the medium vessel without removing the culture plate;
a plurality of upraised cylindrical culture wells formed on the top surface of the culture plate, the culture plate having at least three openings formed extending therethrough in each of the culture wells, at least two of the openings located generally on opposite sides of the culture well; and
an elongated filter paper wick for each culture well formed of flat, planar, non-rigid porous fibrous material, the wick folded to form a central culture host portion overlying and resting for physical support on the top of the culture plate in the culture well and also folded to form legs to extend downwardly through the two opposite of the openings to depend into liquid medium in the medium vessel so that liquid medium will be transported by capillary action to the culture host portion of the wick upon which a tissue culture can be directly placed in each culture well, the other opening in the culture plate in each culture well allowing excess liquid medium in the culture well to drain back into the medium vessel.

2. A plant tissue culture device as claimed in claim 1 wherein the culture plate is mounted on vertical supports extending downwardly to rest on the bottom of the medium vessel.

3. A plant tissue culture device as claimed in claim 2 wherein adjustable connection means join the vertical supports to the culture plate for allowing the height at which the culture plate is mounted to be selectively changed to vary the distance between the culture plate and the liquid level in the vessel to vary the moisture level to which the tissue cultures are exposed.

4. A plant tissue culture device as claimed in claim 3 wherein the vertical supports are hollow vertical cylinders with spaced pairs of horizontal adjustment holes provided therein and wherein the connection means are pegs inserted into one of the pairs of adjustment holes in the vertical supports.

5. A plant tissue culture device as claimed in claim 1 further including a cover plate to cover the top of the medium vessel with the culture plate enclosed therein.

* * * * *